United States Patent [19]

Marsham

[11] 4,338,316

[45] Jul. 6, 1982

[54] 9-ARYLOXY PROSTANE DERIVATIVES

[75] Inventor: Peter R. Marsham, Poynton, England

[73] Assignee: Imperial Chemical Industries Limited, London, England

[21] Appl. No.: 79,176

[22] Filed: Sep. 26, 1979

[30] Foreign Application Priority Data

Oct. 24, 1978 [GB] United Kingdom ............... 41771/78

[51] Int. Cl.$^3$ ................... C07C 177/00; A61K 31/557
[52] U.S. Cl. ..................................... 424/250; 562/465; 562/471; 260/501.1; 562/470; 564/52; 260/501.13; 564/169; 564/189; 260/501.15; 568/31; 568/32; 544/235; 568/630; 568/632; 544/283; 568/634; 568/656; 544/349; 424/251; 424/256; 544/356; 424/258; 424/269; 546/339; 424/274; 424/286; 546/341; 424/308; 424/309; 546/344; 548/460; 548/454; 546/176; 549/407; 549/435; 548/250; 549/437; 549/466; 548/253; 548/484; 548/486; 549/49; 549/58; 549/355; 549/399; 560/21; 560/24; 560/32; 560/55; 560/60; 560/106; 560/111; 560/115; 560/162; 562/434; 562/438; 562/452; 562/455

[58] Field of Search ..................... 560/55, 60, 61, 106, 560/62, 111, 162, 115; 562/465, 470, 471, 434, 438, 452, 455; 564/52, 169, 189; 568/31, 32, 630, 632, 634, 656; 260/326.13, 326.16, 346.22, 501.1, 501.13, 501.15; 544/235, 283, 349, 356; 546/339, 341, 344, 176; 548/250, 253; 549/49, 58; 424/250, 251, 256, 258, 269, 274, 286, 308, 309

[56] References Cited

PUBLICATIONS

Derwent Abstract 43880v/24, DT 2259-260, 6/6/74.

*Primary Examiner*—Paul J. Killos
*Attorney, Agent, or Firm*—Cushman, Darby & Cushman

[57] ABSTRACT

The disclosure relates to 9β-aryloxy prostane derivatives, for example 16-(3-chlorophenoxy)-11α,15α-dihydroxy-16-methyl-9β-phenoxy-18,19,20-trinor-5-cis,13-trans-prostadienoic acid, which possess high activity as abortifacients, cervical softeners, inducers of parturition or inhibitors of gastric acid production in mammals. These properties are typical of prostaglandin analogues of the E series, but chemically the new 9β-aryloxy prostane derivatives are prostaglandin F series analogues and are therefore more stable than the E series analogues previously used for the above purposes. The new derivatives are manufactured by known analogy processes, and are formulated in conventional manner.

6 Claims, No Drawings

9-ARYLOXY PROSTANE DERIVATIVES

This invention relates to prostane derivatives, and in particular it relates to prostane derivatives which possess high activity as abortifacients, cervical softeners or inducers of parturition, and also as inhibitors of the production of gastric acid in mammals.

In humans, prostaglandins of the E-series, for example prostaglandin $E_1$, prostaglandin $E_2$, 15-methyl prostaglandin $E_2$ and 16,16-dimethyl prostaglandin $E_2$, have generally proved to be more potent abortifacients and cervical softeners, and, if given in appropriate dosages, have tended to cause fewer gastrointestinal problems, than prostaglandins of the F-series, such as prostaglandin $F_{2\alpha}$ or 15-methyl prostaglandin $F_{2\alpha}$. An important disadvantage of the E-series compounds for these uses is their inherent chemical instability, involving elimination of the 11-hydroxy radical to form prostaglandins of the A-series. F-series prostaglandins are not susceptible to 11-hydroxy elimination. The present invention, therefore, provides prostaglandin analogues which are chemically stable, but which possess the high activity, as abortifacients or inducers of parturition, of the E-series prostaglandins.

Thus, according to the invention, there is provided a prostane derivative of the formula:

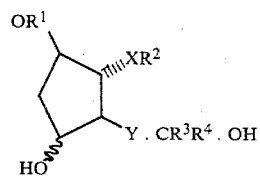

wherein:

$R^1$ is a phenyl or naphthyl radical optionally substituted by one or more halogen atoms, amino, carboxy, hydroxy, hydroxymethyl, nitro, phenyl or trifluoromethyl radicals, 1–4C alkyl, alkoxy, or alkanoylamino radicals 2–5C alkoxycarbonyl or di(1–3C alkyl)amino radicals, or a pyridyl, quinolyl, indolyl, benzo[b]furanyl, benzo[b]thienyl, pyridazinyl, pyrimidinyl or pyrazinyl radical optionally substituted by one or more halogen atoms or 1–4C alkyl radicals;

X is a hexa-1,6-diyl, hex-2-en-1,6-diyl, hexa-2,5-dien-1,6-diyl, hexa-3,5-dien-1,6-diyl, hex-3-en-1,6-diyl or hex-5-trans-en-1,6-diyl radical, in each of which C-1 of the hexyl radical is bonded to the cycopentane ring;

$R^2$ is a carboxy, hydroxymethyl, 5-indanyloxycarbonyl, 4-biphenylyloxycarbonyl or 5-tetrazolyl radical;

a radical of the formula —CO—NHR$^5$ wherein R$^5$ is a 2–8C alkanoyl radical, a 4–8C cycloalkanoyl radical, a 7–11C aroyl or substituted aroyl radical in which the substituent is a halogen atom or a methyl or methoxy radical, a 1–7C alkylsulphonyl radical or an arylsulphonyl or substituted arylsulphonyl radical in which the substituent is a halogen atom or a methyl or methoxy radical;

a radical of the formula —CO.OR$^6$ wherein R$^6$ is a 1–8C alkyl radical, a 4–8C cycloalkyl radical, a phenyl or substituted phenyl radical in which the substituent is 1 to 3 chlorine atoms or 1–4C alkyl radicals, or an ethyl radical substituted in the β-position by 1 to 3 chlorine, bromine or iodine atoms;

a radical of the formula —CO.O.CHR$^7$.COR$^8$ wherein R$^7$ is a hydrogen atom or a benzyl radical and R$^8$ is a phenyl, 4-bromophenyl, 4-biphenylyl, 4-nitrophenyl, 4-benzamidophenyl or 2-naphthyl radical;

a radical of the formula —CH$_2$O.CO(NH)$_m$R$^9$ wherein m is 0 or 1 and R$^9$ is a 1–10C alkyl or halogenoalkyl radical, a 2–10C alkoxyalkyl radical, a ω-carboxy-1–6C-alkyl radical or a phenyl or naphthyl radical optionally substituted by one or more halogen atoms, nitro or phenyl radicals or 1–5C alkyl, alkoxy or halogenoalkyl radicals; or a radical of the formula —COOR$^{10}$ wherein R$^{10}$ is:
—W—NH—CO—CH$_3$
—W—NH—CO—Ph
—W—NH—CO—W—NH—CO—CH$_3$
—W—NH—CO—W—NH—CO—Ph
—W—NH—CO—NH$_2$
—W—Ph
—W—C(Ph)$_3$
—W—CH$_2$—CH(CONH$_3$)—NH—CO—CH$_3$
—W—CH$_2$—CH(CONH$_2$)—NH—CO—Ph
—W—CH=N—NH—CO—NH$_2$
—W—CO—CH$_3$
—W—CO—NH$_2$
—W—CO—NH—W—C(Ph)$_3$
—W—COO—CH$_3$
—W—OOC—Ph
—W—OOC—W—NH—CH$_3$

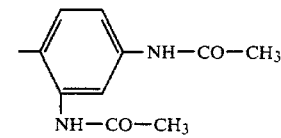

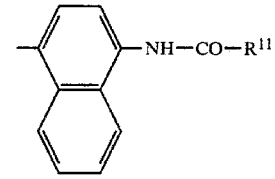

wherein W is a 1,4-phenylene radical and R$^{11}$ is a methyl, phenyl or amino radical;

Y is an ethylene or trans-vinylene radical;

R$^3$ is a hydrogen atom or a 1–4C alkyl radical;

R$^4$ is a 3–8C alkyl radical;

a phenyl, benzyl, phenyl(2–4C alkyl), or phenylethynyl radical optionally substituted in the phenyl ring by one or more halogen atoms, hydroxy, nitro or phenyl radicals, 1–4C alkyl, alkoxy, halogenoalkyl or alkanoylamino radicals, a 2–4C alkenyl or alkenyloxy radicals or di(1–3C alkyl)amino radicals;

a radical of the formula —CR$^{12}$R$^{13}$.OR$^{14}$ wherein R$^{12}$ and R$^{13}$ are each a hydrogen atom or a 1–4C alkyl radical, and R$^{14}$ is a 1–4C alkyl radical or a phenyl or naphthyl radical optionally substituted as defined immediately above;

a radical of the formula —CR$^{12}$R$^{13}$OR$^{15}$, wherein R$^{12}$ and R$^{13}$ have the meanings stated above, or a radical of the formula —R$^{15}$, wherein R$^{15}$ is a radical which is derived from an aromatic 5-membered ring containing one, or two non-adjacent, nitrogen heteroatoms or one nitrogen and one non-adjacent sulphur heteroatoms, or an aromatic fused benzo-homologue thereof, or an aromatic 6-membered ring containing one, or two non-adjacent, heteroatoms or a fused benzo-homologue thereof, or from indoline, pyridine, benzo[b]furan, thiophen or benzo[b]thiophen, which radical is optionally substituted by one or more halogen atoms or 1-4C alkyl radicals;

a radical of the formula $-CR^{12}R^{13}.OR^{14}$ wherein $CR^{12}R^{13}$ together form a 4-6C cycloalkylene radical and $R^{14}$ is a 1-4C alkyl radical or a phenyl or naphthyl radical as defined above; a 4-6C cycloalkyl radical bearing a 1-(2-7C alkyl) substituent; or a radical of the formula:

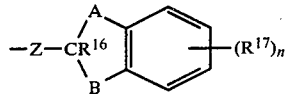

Z is a direct bond or an alkylidene radical of 1 to 5 carbon atoms; either A is an alkylidene radical of 1 to 5 carbon atoms or an ethylene radical, and B is a direct bond, an oxygen or sulphur atom, or an alkylidene radical of 1 to 5 carbon atoms, or A is an oxygen atom and B is an oxygen atom, an alkylideneoxy radical of 1 to 5 carbon atoms wherein the oxygen atom is linked directly to the benzene ring, or an alkylidene(alkylimino) radical [alkylidene-N(alkyl)-] wherein the alkylidene radical is of 1 to 5 carbon atoms and the alkyl radical is of 1 to 4 carbon atoms, and wherein the nitrogen atom is linked directly to the benzene ring; $R^{16}$ is a hydrogen atom or an alkyl radical of 1 to 4 carbon atoms, or $CR^{16}$ together with an adjacent carbon atom of A or B forms a double bond; $R^{17}$ is a halogen atom, or an alkyl, alkoxy or halogenoalkyl radical of 1 to 3 carbon atoms, and n is 0, 1 or 2;

and for those compounds which contain a carboxy radical, the pharmaceutically acceptable salts thereof.

A suitable value for the halogen substituent in $R^1$, $R^9$ or $R^{14}$ when it is a phenyl radical, in $R^1$ or $R^{14}$ when it is a naphthyl radical, in $R^4$ when it is a phenyl, benzyl, phenyl(2-4C alkyl) or phenylethynyl radical or a radical of the formula II as defined above, in $R^5$ when it is an aroyl radical or in $R^{15}$ is, for example, a chlorine, fluorine, bromine or iodine atom, especially a chlorine or fluorine atom, and particularly a chlorine atom.

A suitable value for a 1-4C alkyl substituent in $R^1$ when it is a phenyl or naphthyl radical, in $R^4$ when it is a phenyl, benzyl, phenyl(2-4C alkyl) or phenylethynyl radical, or a radical of the formula II as defined above, in $R^6$ when it is a phenyl radical, in $R^{14}$ when it is a phenyl radical, or in $R^{15}$, or for $R^3$, $R^{12}$, $R^{13}$ or $R^{14}$ when it is a 1-4C alkyl radical is, for example, a methyl, ethyl, n-propyl, isopropyl, n-butyl, s-butyl, t-butyl or isobutyl radical.

A suitable value for $R^6$ when it is a 1-8C alkyl radical is, for example, a methyl, ethyl, propyl, butyl, phenyl, hexyl, heptyl or octyl radical.

A suitable value for $R^9$ when it is a 1-10C alkyl radical is, for example, a methyl ethyl, propyl, butyl, pentyl, hexyl, heptyl, octyl, nonyl or decyl radical.

A suitable value for a 1-5C alkyl substituent in $R^9$ when it is a phenyl or naphthyl radical is, for example, a methyl, ethyl, propyl, butyl or pentyl radical.

A suitable value for $R^4$ when it is a 3-8C alkyl radical is, for example, a propyl, butyl, pentyl, hexyl, heptyl or octyl radical, and particularly a straight-chain such radical.

A suitable value for a 2-7C alkyl substituent in $R^4$ when it is a 4-6C cycloalkyl radical is, for example, an ethyl, propyl, butyl, pentyl, hexyl or heptyl radical.

A suitable value for a 1-4C alkoxy substituent in $R^1$ when it is a phenyl or naphthyl radical, in $R^4$ when it is a phenyl, benzyl or phenylethynyl radical or a radical of the formula II as defined above, in $R^{14}$ when it is a phenyl or naphthyl radical or in $R^{15}$ is, for example, a methoxy, ethoxy, n-propoxy, isopropoxy, n-butoxy, s-butoxy, t-butoxy or isobutoxy radical.

A suitable value for a 1-5C alkoxy substituent in $R^9$ when it is a phenyl or naphthyl radical is, for example, a methoxy, ethoxy, propoxy, butoxy or pentyloxy radical.

A suitable value for a 1-4C alkanoylamino substituent in $R^1$ when it is a phenyl or naphthyl radical or in $R^4$ when it is a phenyl, benzyl or phenylethynyl radical is, for example, a formamido, acetamido, propionamido or butyramido radical.

A suitable value for a 2-5C alkoxycarbonyl substituent in $R^1$ when it is a phenyl or naphthyl radical is, for example, a methoxycarbonyl, ethoxycarbonyl, propoxycarbonyl or butoxycarbonyl radical.

A suitable value for $R^5$ when it is a 2-8C alkanoyl radical is, for example, an acetyl, propionyl, butyryl, valeryl, hexanoyl, heptanoyl or octanoyl radical.

A suitable value for $R^5$ when it is a 4-8C cycloalkanoyl radical is a cyclopropylcarbonyl, cyclobutylcarbonyl, cyclopentylcarbonyl, cyclohexylcarbonyl or cycloheptylcarbonyl radical; and for $R^6$ when it is a 4-8C cycloalkyl radical is a cyclobutyl, cyclopentyl, cyclohexyl, cycloheptyl or cyclooctyl radical.

A suitable value for $R^5$ when it is a 7-11C aroyl radical is, for example, a benzoyl or naphthoyl radical, optionally substituted as defined herein.

A suitable value for $R^5$ when it is a 1-7C alkylsulphonyl radical is, for example, a methylsulphonyl, ethylsulphonyl, propylsulphonyl, butylsulphonyl, pentylsulphonyl, hexylsulphonyl or heptylsulphonyl radical.

A suitable value for $R^5$ when it is an arylsulphonyl radical is, for example, a phenylsulphonyl radical, optionally substituted as defined herein.

A suitable value for $R^6$ when it is an ethyl radical substituted in the β-position with 1 to 3 chlorine, bromine or iodine atoms is, for example, a 2-chloroethyl or 2,2,2-trichloroethyl radical.

A suitable value for $R^9$ when it is a 2-10C alkoxyalkyl radical is, for example, a methoxymethyl, ethoxymethyl, straight- or branched-chain propoxymethyl, butoxymethyl or pentyloxymethyl, 2-methoxyethyl or 2-ethoxyethyl radical.

A suitable value for $R^9$ when it is a 1-10C halogenoalkyl radical is, for example, a 1-10C alkyl radical bearing one or more chlorine, bromine or fluorine atoms as substituents, and a suitable value for a 1-5C halogenoalkyl substituent in $R^9$ when it is a phenyl or naphthyl radical is, for example, a 1-5C alkyl radical bearing one or more chlorine, bromine or fluorine atoms as substituents.

A suitable value for $R^9$ when it is an ω-carboxy-1-6C alkyl radical is, for example, a carboxymethyl, 2-carboxyethyl, 3-carboxypropyl, 4-carboxybutyl or 5-carboxypentyl radical.

A suitable value for a 2-4C alkenyl or alkenyloxy substituent in $R^4$ when it is a phenyl, benzyl, phenyl(-

2-4C alkyl) or phenylethynyl radical is, for example, a vinyl, allyl or allyloxy radical.

A suitable value for a di(1–3C alkyl)amino substituent in $R^1$ or $R^4$ when it is a phenyl, benzyl, phenyl(2–4C alkyl) or phenylethynyl radical is, for example, a dimethylamino, diethylamino, dipropylamino or ethylmethylamino radical.

A suitable pharmaceutically acceptable salt of a compound which contains a carboxy radical is, for example, the ammonium, alkylammonium containing 1 to 4 1–6C alkyl radicals, alkanolammonium containing 1 to 3 2-hydroxyethyl radicals, or alkali metal salt, for example the ammonium, triethylammonium, ethanolammonium, diethanolammonium, sodium or potassium salt.

Particular compounds of the invention are 16-(3-chlorophenoxy)-11α,15α-dihydroxy-16-methyl-9β-phenoxy-18,19,20-trinor-5-cis,13-trans-prostadienoic acid, 11α,15α-dihydroxy-16,16-dimethyl-9β-phenoxy-5-cis,13-trans-prostadienoic acid, 9β,16-bis(3-chlorophenoxy)-16-methyl-18,19,20-trinor-5-cis,13-trans-prostadien-1,11α,15α-triol, 11α,15α-dihydroxy-9β-phenoxy-5-cis,13-trans-prostadienoic acid, 9β,16-bis(3-chlorophenoxy)-11α,15α-dihydroxy-16-methyl-18,19,20-trinor-5-cis,13-trans-prostadienoic acid and 9β-(5-chloropyrid-2-yloxy)-11α,15-dihydroxy-16,16-dimethyl-5-cis,13-trans-prostadienoic acid.

The prostane derivatives of the formula I may be manufactured by processes which are known in themselves for the manufacture of chemically analogous compounds. Examples of such chemical analogy processes are:

(a) the hydrolysis with an acid, for example acetic acid or toluene-p-sulphonic acid, of a bis(tetrahydropyran-2-yl ether) of the formula:

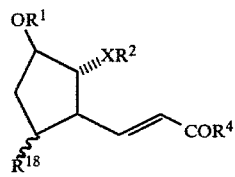

wherein $R^1$, $R^2$, $R^3$, $R^4$, X and Y have the meanings stated above and THP is a tetrahydropyran-2-yl radical;

(b) for those compounds wherein $R^3$ is a hydrogen atom, the reduction, for example with zinc borohydride, sodium borohydride, aluminium triisopropoxide or di-isobornyloxyaluminium isopropoxide, of a ketone of the formula:

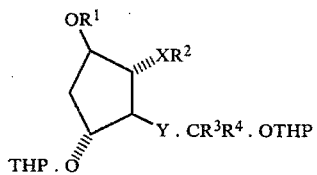

wherein $R^1$, $R^2$, $R^4$, X and Y have the meanings stated above and $R^{18}$ is a hydroxy or protected hydroxy radical, for example a 2–14C carboxylic acyloxy radical such as an acetoxy, benzoyloxy or 4-phenylbenzoyloxy radical, a tetrahydropyran-2-yloxy radical or a tri(1–4C alkyl)silyloxy, tribenzylsilyloxy or triphenylsilyloxy radical, whereafter when $R^{18}$ is a protected hydroxy radical, the protecting group is hydrolysed;

(c) for those compounds wherein $R^3$ is an alkyl radical, the reaction of a ketone of the formula IV wherein $R^1$, $R^2$, $R^4$, $R^{18}$ and X have the meanings stated above, with a 1–4C alkyl magnesium halide, whereafter when $R^{18}$ is a protected hydroxy group the protecting group is hydrolysed;

(d) the hydrolysis of an ester of the formula:

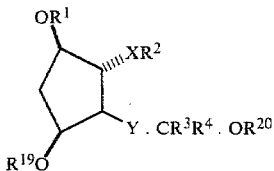

wherein $R^1$, $R^2$, $R^3$, $R^4$, X and Y have the meanings stated above, $R^{19}$ is a 2–14C carboxylic acyl radical such as an acetyl, benzoyl or 4-phenylbenzoyl radical, and $R^{20}$ is a hydrogen atom or a 2–14C carboxylic acyl radical, as defined above;

whereafter, if desired, particular substituents $R^2$ in the products thus obtained may be transformed to other such substituents as defined above, or the 11-hydroxy group in the products thus obtained may be epimerised, or a 2-trans double bond may be introduced, by conventional methods in actual use or known in the literature of organic chemistry.

In process (b), it is to be understood that, when the reduction is carried out with an isopropoxide reagent, the product obtained is predominantly that wherein Y is a trans-vinylene radical, whereas, when the reduction is carried out with a borohydride reducing agent, the product contains a substantial proportion of the product wherein Y is an ethylene radical, which may be isolated in conventional manner, for example by chromatography.

Examples of such optional transformations on the primary products of the above process are:

(i) esterification of a carboxy-substituted compound of the formula I to give an alkoxycarbonyl-substituted compound of the formula I, for example by reacting the carboxylic acid with a diazoalkane or by reacting a salt of the carboxylic acid with an alkyl halide;

(ii) esterification of a compound of the formula I wherein $R^2$ is a carboxy radical to give a compound of the formula I wherein $R^2$ is a 5-indanyloxycarbonyl radical, a radical of the formula —COOR$^6$ or —COOR$^{10}$ as defined above or a 4-biphenylyloxycarbonyl radical, for example by reacting a mixed anhydride of the carboxylic acid with 5-indanol or with the appropriate alcohol or phenol, or reacting the carboxylic acid with 5-indanol or the appropriate alcohol or phenol in the presence of dicyclohexylcarbodi-imide;

(iii) reduction of a compound of the formula I wherein $R^2$ is a radical of the formula —COOR$^6$, to give a compound of the formula I wherein $R^2$ is a hydroxymethyl radical;

(iv) the hydrolysis of a compound of the formula I wherein $R^2$ is a radical of the formula —CONHR$^5$, —COOR$^6$, —CO.OCHR$^7$.COR$^8$ or —COOR$^{10}$ as defined above, or a 5-indanyloxycarbonyl or 4-biphenylyloxycarbonyl radical to give a compound of the formula I wherein $R^2$ is a carboxy radical;

(v) introduction of a 2-trans double bond, for example by the reaction of a compound of the formula I wherein X is a hex-1,6-diyl, hex-2-en-1,6-diyl or hex-3-en-1,6- diyl radical with a lithium di(1–6C alkyl)amide to give a 2-lithio derivative, converting the 2-lithio derivative to a 2-phenylthio or 2-phenylselenyl derivative, and decomposition of the 2-phenylthio or 2-phenylselenyl derivative to form a compound of the formula I wherein X is hex-5-trans-en-1,6-diyl, hexa-2,5-dien-1,6-diyl or hexa-3,5-dien-1,6-diyl radical;

(vi) epimerisation of the 11-hydroxy group, for example by reaction of an 11α-hydroxy compound of the formula I with (a) an ester or amide of azobiscarboxylic acid, such as azobisformamide or diethyl azodicarboxylate, (b) tri(3–8C alkyl)phosphine, triphenylphosphine, triphenylarsine, triphenylstibine or hexamethylphosphorus triamide and (c) a carboxylic acid, such as acetic or benzoic acid, followed by hydrolysis of the 11β-acyloxy compound thus formed to give the epimeric 11β-hydroxy compound of the formula I; and (vii) reaction of a compound of the formula I wherein $R^2$ is a carboxy radical with a base, to give a pharmaceutically acceptable salt, as defined above.

Starting materials of the formula III, wherein X is a hex-2-cis-en-1,6-diyl radical as defined above, may be obtained by the reaction of a known lactol VI with a (4-carboxybutyl)-triphenylphosphonium salt, for example the bromide, in the presence of a strong base to give an acid VII. The acid VII is reacted with diazomethane to give a methyl ester VIII, and the methyl ester VIII is treated with triphenylphosphine, diethyl azodicarboxylate and a phenol, $R^1OH$, to give a starting material of the formula III in which $R^2$ is a methoxycarbonyl radical, $R^1$, $R^3$, $R^4$ and Y have the meanings stated above, and X is a hex-2-cis-en-1,6-diyl radical as defined above.

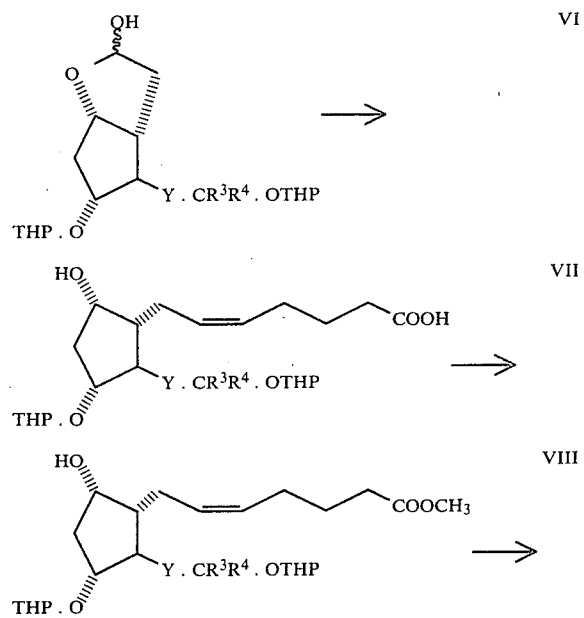

III (X = hex-2-cis-en-1,6-diyl, $R^2$ = COOCH₃)
THP = tetrahydropyran-2-yl

Corresponding starting materials of the formula III wherein $R^2$ is a 5-tetrazolyl radical may be obtained similarly, but using a (4-tetrazol-5′-ylbutyl)triphenylphosphonium salt in place of a (4-carboxybutyl)triphenylphosphonium salt.

Corresponding starting materials of the formula III wherein $R^2$ is a radical of the formula —COOR⁶ or —COOR¹⁰ as defined above may be obtained similarly by converting the acid VII to the appropriate ester, analogous to VIII, in which the —COOCH₃ group is replaced by —COOR⁶ or —COOR¹⁰.

Corresponding starting materials of the formula III wherein $R^2$ is a carboxy radical may be obtained by hydrolysis of a starting material of the formula III in which $R^2$ is a methoxycarbonyl radical.

Corresponding starting materials of the formula III wherein $R^2$ is a radical of the formula —CONHR⁵ in which $R^5$ is an alkanoyl, cycloalkanoyl, aroyl or substituted aroyl radical as defined above may be obtained by reacting a starting material of the formula III wherein $R^2$ is a carboxy radical with an isocyanate of the formula R⁵NCO. Alternatively any starting material of the formula III wherein $R^2$ is a radical of the formula —CONHR⁵ may be obtained by reacting a lactol VI with a phosphonium salt of the formula Ph₃P.(CH₂)₄CONHR⁵, and using the product thus obtained in place of the acid VII in the subsequent stages of the synthesis.

Corresponding starting materials of the formula III wherein $R^2$ is a 5-indanyloxycarbonyl or 4-biphenylyloxycarbonyl radical, or a radical of the formula —COOR⁶ or —COOR¹⁰ as defined above, may alternatively be obtained from the starting material of the formula III wherein $R^2$ is a carboxy radical by reaction with 5-indanol or the appropriate alcohol or phenol in a mixed anhydride reaction, or in the presence of dicyclohexylcarbodi-imide.

Corresponding starting materials of the formula III wherein $R^2$ is a radical of the formula —CO.O.CHR⁷.COR⁸ as defined above may be obtained from the starting material of the formula III wherein $R^2$ is a carboxy radical by converting it to a salt, for example the sodium salt, and reacting the sodium salt with the appropriate phenacyl halide, R⁸CO.CHR⁷.O.CO.halogen.

Corresponding starting materials of the formula III wherein $R^2$ is a hydroxymethyl radical may be obtained by the reduction, for example with lithium borohydride or lithium aluminium hydride, of the starting material of the formula III wherein $R^2$ is a methoxycarbonyl radical.

Corresponding starting materials of the formula III wherein $R^2$ is a radical of the formula —CH₂O.CO(NH)ₘR⁹ as defined above may be obtained from the starting material of the formula III wherein $R^2$ is a hydroxymethyl radical by reaction thereof with an acylating agent derived from the carboxylic acid R⁹(NH)ₘ.COOH, for example an acyl halide, an acid anhydride, a mixed anhydride or an isocyanate, R⁹.NCO.

Corresponding starting materials of the formula III wherein X is a hex-2-trans-en-1,6-diyl radical may be obtained similarly, except that in the reaction of the lactol VI with a triphenylphosphonium salt, butyllithium is used as the strong base and sulpholane as the solvent to give a mixture of the cis acid VII and the corresponding trans acid, which may be separated from the mixture, for example by chromatography, and used in place of the cis acid VII in the subsequent stages of the synthesis.

Corresponding starting materials of the formula III wherein X is a hexa-1,6-diyl radical as defined above may be obtained by selective catalytic hydrogenation of an ester VIII, and using the hydrogenated ester in place of VIII in the remaining stage of the reaction sequence described above.

Starting materials of the formula III wherein X is a hex-3-cis-en-1,6-diyl radical as defined above may be obtained by reacting the lactol VI with methylenetriphenylphosphorane (Ph₃P:CH₂) to give an olefin IX which is treated with triphenylphosphine, diethyl azodicarboxylate and a phenol R¹OH to give the olefin X, and the olefin X is hydroxylated with diborane followed by alkaline hydrogen peroxide to give the alcohol XI. The alcohol XI is oxidised with chromium trioxide/pyridine complex to the aldehyde XII, and the aldehyde XII is reacted with a (3-carboxypropyl)triphenylphosphonium salt, for example the iodide, in the presence of a strong base, to give a starting material of the formula III in which $R^2$ is a carboxy radical, $R^1$, $R^3$, $R^4$ and Y have the meanings stated above, and X is a hex-3-cis-en-1,6-diyl radical as defined above.

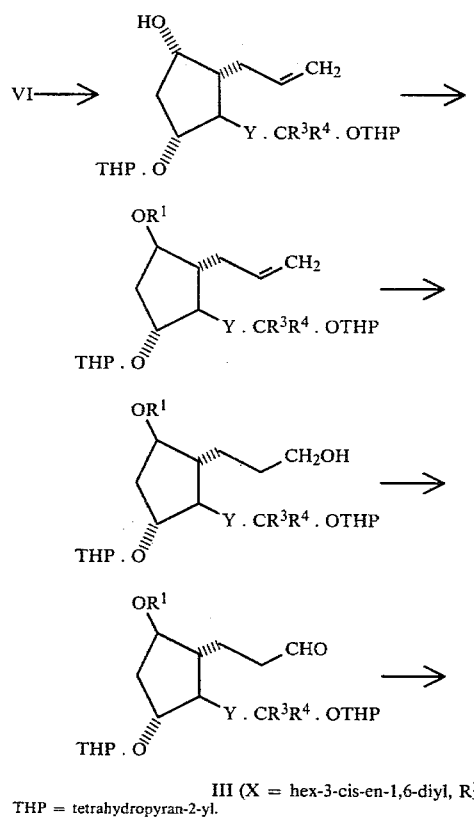

Corresponding starting materials of the formula III wherein $R^2$ is a 5-tetrazolyl radical may be obtained similarly, but using a (3-tetrazol-5'-ylpropyl)triphenylphosphonium in place of a (3-carboxypropyl)triphenylphosphonium salt.

Corresponding starting materials of the formula III wherein $R^2$ is a radical of the formula —COOR⁶, —COOR¹⁰, —CONHR⁵, or —CO.O.CHR⁷.COR⁸, or a 5-indanyloxycarbonyl or 4-biphenylyloxycarbonyl radical may be obtained from a starting material of the formula III wherein $R^2$ is a carboxy radical in the same way that the analogous compounds in the X=hex-2-cis-en-1,6-diyl series are obtained from the analogous $R^2$=carboxy starting materials, as described above. Similarly, corresponding starting materials of the formula III wherein $R^2$ is a hydroxymethyl radical or a radical of the formula —CH₂O.CO(NH)ₘR⁹ are obtained in an analogous manner to the corresponding compounds in the X=hex-2-cis-en-1,6-diyl series described above.

Corresponding starting materials of the formula III wherein X is a hex-3-trans-en-1,6-diyl radical as described above may be obtained similarly, except that in the reaction of the aldehyde XII with a triphenylphosphonium salt, butyllithium is used as the strong base and sulpholane as the solvent to give a mixture of the cis starting material III and the trans isomer, from which the latter may be separated, for example by chromatography.

Starting materials of the formula IV, wherein X is a hex-2-cis-en-1,6-diyl radical as defined above, may be obtained by treating the acid XIII with diazomethane to give the methyl ester XIV which is then treated with triphenylphosphine, diethyl azodicarboxylate and a phenol R¹OH to give a tetrahydropyranyl ether XV, and the ether XV is hydrolysed to remove the tetrahydropyranyl group, giving the alcohol XVI. The alcohol XVI is esterified with 4-phenylbenzoyl chloride to give the 4-phenylbenzoate XVII, and XVII is then hydrolysed with acid to give the aldehyde XVIII, which is reacted with a phosphonate of the formula (CH₃O)₂PO.CH₂COR⁴ to give a starting material of the formula IV in which $R^2$ is a methoxycarbonyl radical, $R^1$, $R^3$ and $R^4$ have the meanings stated above, X is a hex-2-cis-en-1,6-diyl radical

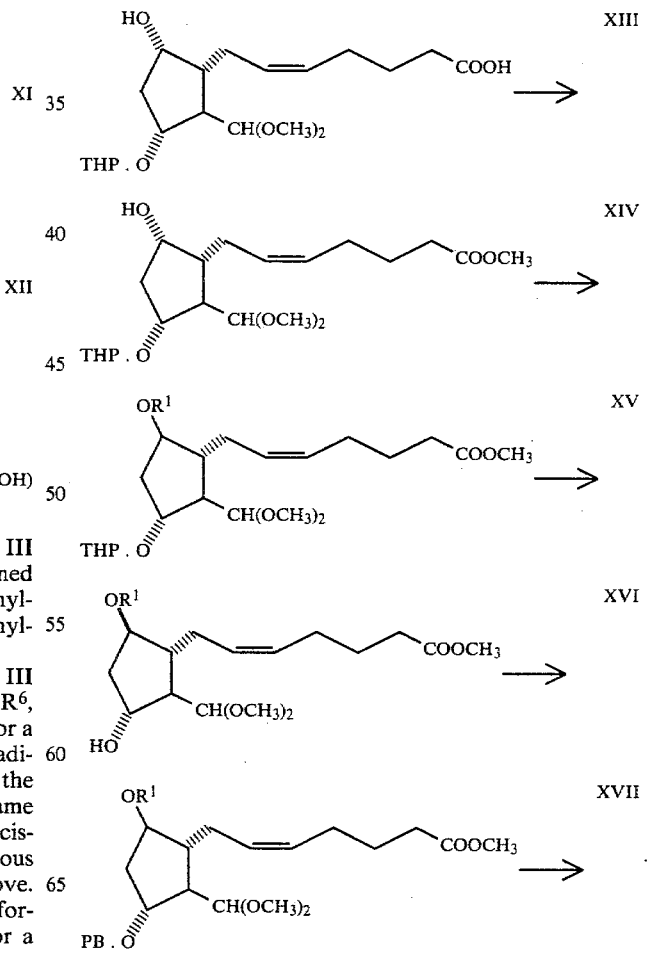

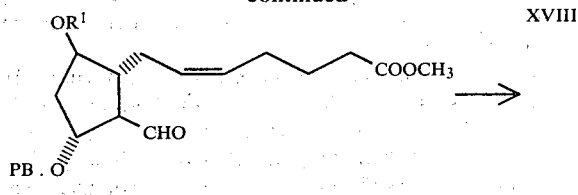

IV (X = hex-2-cis-en-1,6-diyl, $R^2$ = COOCH$_3$)
PB = 4-phenylbenzoyl, THP = tetrahydropyran-2-yl.

as defined above, and $R^{17}$ is a 4-phenylbenzoyloxy radical.

Corresponding starting materials of the formula IV wherein $R^{15}$ is another carboxylic acyloxy radical as defined above or a silyloxy radical as defined above may be obtained by using an appropriate acylating or silylating reagent in the reaction with the alcohol XVI, in place of 4-phenylbenzoyl chloride.

Corresponding starting materials of the formula IV wherein $R^{17}$ is a hydroxy radical may be obtained by omitting the esterification step XVI to XVII, and using the alcohol XVI in place of the phenylbenzoate XVII in the subsequent stages of the synthesis.

Corresponding starting materials of the formula IV wherein $R^2$ is a radical of the formula —COOR$^6$, —COOR$^{10}$, —CONHR$^5$ or —CO.O.CHR$^7$.COR$^8$ as defined above, or a 5-indanyloxycarbonyl or 4-biphenylyloxycarbonyl radical may be obtained by esterification or amidation of the acid XIII, or of a corresponding starting material of the formula IV wherein $R^2$ is a carboxy radical, in the manner described above for analogous compounds.

Corresponding starting materials of the formula IV wherein $R^2$ is a carboxy radical may be obtained by hydrolysis of a starting material of the formula IV wherein $R^2$ is a methoxycarbonyl radical.

Corresponding starting materials of the formula IV wherein $R^2$ is a radical of the formula —CH$_2$O.CO(NH)$_m$R$^9$ as defined above may be obtained by reduction, for example with lithium aluminium hydride, of the ester XV and esterification of the alcohol thus obtained with an acylating agent derived from the carboxylic acid $R^9(NH)_m$.COOH as defined above, and using the ester thus obtained in place of the methyl ester XV in the subsequent stages of the synthesis.

Corresponding starting materials of the formula IV wherein X is a hex-2-trans-1,6-diyl radical as defined above may be obtained similarly using the trans-analogue of the acid XIII in place of the acid XIII in the reaction sequence described above.

Corresponding starting materials of the formula IV wherein X is a hexa-1,6-diyl radical as described above may be obtained by catalytic hydrogenation of any compound XIV to XVII, and using the hydrogenated compound in place of the corresponding compound XIV to XVII in the reaction sequence described above.

Starting materials of the formula IV wherein X is a hex-3-cis-en-1,6-diyl radical as defined above may be obtained by treating the olefin XIX with triphenylphosphine, diethyl azodicarboxylate and a phenol $R^1OH$ to give an olefin XX, which is hydroxylated with diborane and alkaline hydrogen peroxide to the alcohol XXI. The alcohol XXI is oxidised with Collins' reagent to the aldehyde XXII, and the aldehyde XXII is reacted with a (3-carboxypropyl)triphenylphosphonium salt in the presence of a strong base to give the acid XXIII, which is converted to the ester XXIV with diazomethane. The ester XXIV is selectively hydrolysed to convert the acetal group to an aldehyde (XXV), and the aldehyde is reacted with a phosphonate (CH$_3$O)$_2$PO.CH$_2$COR$^4$ to give a starting material of the formula IV in which $R^2$ is a methoxycarbonyl radical and X is a hex-3-cis-en-1,6-diyl radical, as defined above.

Corresponding starting materials of the formula IV wherein $R^2$ is a radical of the formula —COOR$^6$, —COOR$^{10}$, —CONHR$^5$ or —CO.O.CHR$^7$.COR$^8$ as defined above, or a 5-indanyloxycarbonyl or 4-biphenylyloxycarbonyl radical may be obtained by esterification or amidation of the acid XXIII or of a corresponding starting material of the formula III wherein $R^2$ is a carboxy radical, in the manner described above for analogous compounds, and using the ester or amide thus obtained in place of the acid XXIII in the remaining stages of the synthesis.

Corresponding starting materials of the formula IV wherein $R^2$ is a carboxy radical may be obtained by hydrolysis of a starting material of the formula IV wherein $R^2$ is a methoxycarbonyl radical.

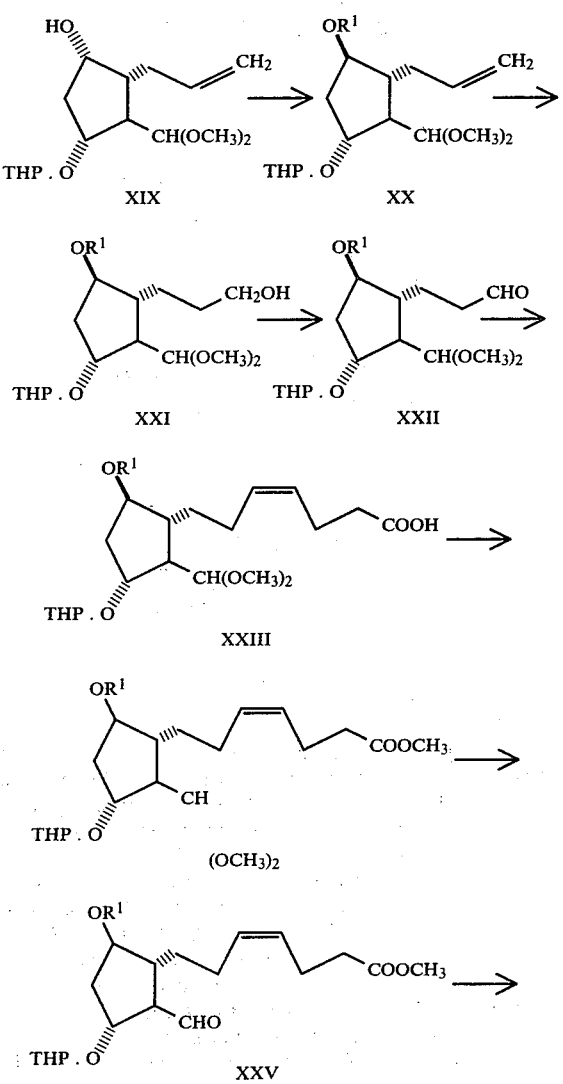

III (X = hex-3-cis-en-1,6-diyl, $R^2$ = COOCH$_3$)
THP = tetrahydropyran-2-yl

Corresponding starting materials of the formula IV wherein $R^2$ is a radical of the formula $-CH_2O\text{-}CO(NH)_mR^9$ as defined above may be obtained by reduction, for example with lithium aluminium hydride, of an ester XXIV, and esterification of the alcohol thus obtained with an acylating agent derived from the carboxylic acid $R^9(NH)_mCOOH$ as defined above, and using the ester so obtained in place of the ester XXIV in the subsequent stages of the synthesis.

Corresponding starting materials of the formula IV wherein X is a hex-3-trans-en-1,6-diyl radical as defined above may be obtained by reaction of the aldehyde XXII with a vinyl magnesium halide or vinyl-lithium to give an unsaturated alcohol XXVI which is heated with triethyl orthoacetate to give an ester XXVII. The ester XXVII is then used in place of the ester XXIV in the subsequent stages of the synthesis described above.

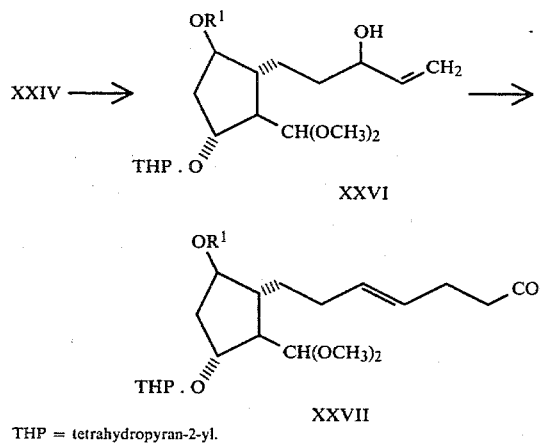

THP = tetrahydropyran-2-yl.

Starting materials of the formula V wherein $R^{19}$ is a hydrogen atom or a carboxylic acyl radical may be obtained by the reaction of a compound of the formula I wherein $R^3$ is respectively a hydrogen atom or an alkyl radical with triphenylphosphine, diethyl azodicarboxylate and carboxylic acid $R^{18}OH$.

It is to be understood, of course, that an optically active prostane derivative of the invention may be obtained either by resolving the corresponding racemate, or by resolving a suitable starting material or other intermediate in the preparative reaction sequence.

As stated above, the novel prostane derivative of the invention inhibits the production of gastric acid in mammals. For example, in an anaesthetised rat, 16-(3-chlorophenoxy)-11α,15α-dihydroxy-16-methyl-9β-phenoxy-18,19,20-trinor-5-cis,13-trans-prostadienoic acid causes a 50% inhibition of histamine-stimulated gastric acid production at an intravenous dose of 17.0 μg./kg.

When a prostane derivative of the invention is to be used for reducing gastric acid production in man, it is to be used in substantially the same way as it is known to use prostaglandin $E_2$ or (15S)- or (15R)-15-methyl-prostaglandin $E_2$ methyl ester for similar purposes. Such prostaglandin analogues have been administered orally, in aqueous solution, at doses of 2.5 to 4.0 mg. for prostaglandin $E_2$, and 100 to 200 μg. for (15S)- and (15R)-15-methyl-prostaglandin $E_2$ methyl ester. The latter compound has been shown to promote healing of gastric ulcers in Chinese subjects when administered orally at 150 μg. in 20 ml. of water at 6 hourly intervals for 2 weeks.

Also as stated above, the novel prostane derivative of the invention may be used to terminate pregnancy or to induce labour or parturition. For example, in a pregnant guinea pig, 16-(3-chlorophenoxy)-11α,15α-dihydroxy-16-methyl-9β-phenoxy-18,19,20-trinor-5-cis,13-trans-prostadienoic acid causes premature parturition when administered as two subcutaneous doses of 30.0 μg. two hours aparts on day 65 of the pregnancy.

When a compound of the invention is to be used, for example for the induction of labour, it is used in the same way as it is known to use the naturally-occurring prostaglandin $E_2$ and $F_2\alpha$, that is to say, by administering a sterile, substantially aqueous solution containing up to 1 mg/ml. of active compound, by intravenous infusion, by transcervical extra-amniotic infusion or intra-amniotic infusion, until labour commences.

Thus according to a further feature of the invention there is provided a pharmaceutical or veterinary composition comprising a prostane derivative of the formula I as defined above, together with a pharmaceutically or veterinarily acceptable diluent or carrier.

The compositions may be in a form suitable for oral administration, for example tablets or capsules, in a form suitable for infusion, for example sterile aqueous or oily solutions or suspensions, or in the form of a suppository, suitable for anal or vaginal use.

A preferred composition is a substantially aqueous solution containing 25 to 150 μg./ml., preferably 75 to 125 μg./ml. of the prostane derivative.

The compositions of the invention may be manufactured by conventional means, and may contain conventional pharmaceutical excipients in addition to the active constituent and the diluent or carrier. The compositions may be stabilised, for example by incorporation of dimethylacetamide, in known manner.

The invention is illustrated but not limited by the following examples. Unless otherwise stated all reactions were carried out at room temperature in an atmosphere of argon. $R_F$ values refer to thin layer chromatography on silica gel plates supplied commercially by Merck of Darmstadt, and the spots were detected either by fluorescence, or by spraying the plates with a solution of ceric ammonium nitrate in sulphuric acid. Preparative layer chromatography was performed on 2.0 mm. or 0.25 mm. thick silica gel plates supplied commercially by Merck of Darmstadt. 'Kieselgel 60' (trade mark) used for dry column chromatography was supplied commercially by Merck of Darmstadt. Before use it was deactivated by the adsorption of 10% w/w of water and then equilibrated by the adsorption of 10% v/w of the eluting solvent. Silica gel M.F.C. (60–120 mesh) used for column chromatography was supplied commercially by Hopkin and Williams. Solutions of products in organic solvents were dried over anhydrous sodium sulphate and evaporated below 40° C. under reduced pressure.

EXAMPLE 1

A solution of methyl 16-(3-chlorophenoxy)-16-methyl-9β-phenoxy-11α,15α-bis(tetrahydropyran-2-yloxy)-18,19,20-trinor-5-cis,13-trans-prostadienoate (100 mg.) and toluene-p-sulphonic acid monohydrate (5 mg.) in methanol (2 ml.) was stirred for one hour. Pyridine (15 μl.) was then added and the solvent was evaporated. Purification of the residue by preparative layer chromatography gave the methyl ester, methyl 16-(3-chlorophenoxy)-11α,15α-dihydroxy-16-methyl-9β-phenoxy- 18,19,20-trinor-5-cis,13-trans-prostadienoate, $R_F=0.34$ (1:1 v/v ethyl acetate/toluene).

A solution of this methyl ester (10.5 mg.) in methanol (1 ml.) was stirred with 1 N aqueous sodium hydroxide (0.10 ml.) for 16 hours and the solvent was then evaporated. The residue was dissolved in water (1 ml.) and acidified to pH 1 by the dropwise addition of 1 N hydrochloric acid, and the aqueous phase was extracted with ethyl acetate (3×5 ml.). The combined ethyl acetate solutions were dried and the solvent was evaporated. The residue was purified by preparative layer chromatography to yield 16-(3-chlorophenoxy)-11α,1-5α-dihydroxy-16-methyl-9β-phenoxy-18,19,20-trinor-5-cis,13-trans-prostadienoic acid as a colourless gum, $R_F=0.63$ (ethyl acetate). The n.m.r. spectrum in hexadeuterioacetone has the following characteristic signals (δ values):

6.75–7.40, 9H, multiplet, aromatic protons
5.76, 2H, multiplet, trans-olefinic protons
5.44, 2H, multiplet, cis-olefinic protons
4.50, 1H, multiplet, >C$\underline{H}$(OPh)
3.90–4.20, 2H, multiplet, >C$\underline{H}$(OH)
1.30, 6H, singlet, >C(C$\underline{H}_3$)$_2$ The mass spectrum of the tris(trimethylsilyl) derivative had (M-methyl)$^+$=729.3215. Calculated for $C_{38}H_{58}O_6Si_3Cl=729.3228$.

The methyl 16-(3-chlorophenoxy)-16-methyl-9β-phenoxy-11α,15α-bis(tetrahydropyran-2-yloxy)-18,19,20-trinor-5-cis-13-trans-prostadienoate used as starting material was prepared as follows:

16-(3-Chlorophenoxy)-9α-hydroxy-16-methyl-11α,1-5α-bis(tetrahydropyran-2-yloxy)-18,19,20-trinor-5-cis,13-trans-prostadienoic acid (359 mg.) was treated for 5 minutes with an excess of ethereal diazomethane. The ether and excess reagent were then distilled off on a water bath at 50° C. and the resulting methyl ester was purified by dry column chromatography on "Kieselgel 60" (50 g.), eluting with 1:1 v/v ethyl acetate/toluene.

A solution of the above methyl ester (80 mg.), triphenylphosphine (63.5 mg.) and phenol (24 mg.) in anhydrous tetrahydrofuran (3 ml.) was stirred during the dropwise addition of a solution of diethyl azodicarboxylate (46.5 mg., 95% pure) in anhydrous tetrahydrofuran (1 ml.). After a further one hour the solvent was evaporated and the residue was chromatographed on a "Florisil" (trade mark) magnesium silicate column (5 g.), eluting with 4:1 v/v toluene/ethyl acetate, to yield the required methyl 16-(3-chlorophenoxy)-16-methyl-9β-phenoxy-11α,15α-bis(tetrahydropyran-2-yloxy)-18,19,20-trinor-5-cis,13-trans-prostadienoate, contaminated with unreacted phenol, which was used without further purification.

The compounds shown in the following table were prepared in a similar manner to that described above, and the required starting materials were also prepared similarly by using the appropriate substituted phenol in the ether formation reaction.

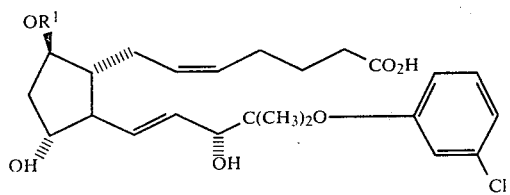

| R$^1$ | $R_F$ (ethyl acetate) | Mass Spectrum of tris(trimethylsilyl) derivative (M-methyl)$^+$ | |
|---|---|---|---|
| | | Found | Calculated |
| 3-chlorophenyl | 0.38 | 763.2800 | 763.2838 |
| 4-chlorophenyl | 0.47 | 763.2823 | 763.2838 |
| 3-trifluoromethylphenyl | 0.45 | 797.3125 | 797.3102 |
| 4-fluorophenyl | 0.47 | 747.3163 | 747.3134 |

EXAMPLE 2

The process described in Example 1 was repeated using methyl 16,16-dimethyl-9β-phenoxy-11α,15-bis(tetrahydropyran-2-yloxy)-5-cis,13-trans-prostadienoic acid in place of methyl 16-(3-chlorophenoxy)-16-methyl-9β-phenoxy-11α,15α-bis(tetrahydropyran-2-yloxy)-18,19,20-trinor-5-cis,13-trans-prostadienoate, to give the C-15 epimers of 11α,15-dihydroxy-16,16-dimethyl-9β-phenoxy-5-cis,13-trans-prostadienoic acid, $R_F=0.50$ and 0.54 (ethyl acetate). The n.m.r. spectrum in hexadeuterioacetone of the more polar C-15 epimer had the following characteristic signals (δ values):

6.75–7.33, 5H, multiplet, aromatic protons
5.64, 2H, multiplet, trans-olefinic protons
5.45, 2H, multiplet, cis-olefinic protons
4.46, 1H, multiplet, >CH(OPh)

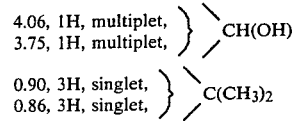

4.06, 1H, multiplet,
3.75, 1H, multiplet, } >CH(OH)

0.90, 3H, singlet,
0.86, 3H, singlet, } >C(CH$_3$)$_2$

The mass spectrum of the tris(trimethylsilyl) derivative of the more polar C-15 epimer had (M-methyl)$^+$=659.3994. Calculated for $C_{36}H_{63}O_5Si_3=659.3983$.

The methyl ester used as starting material was prepared by the process described in the second part of Example 1, using 9α-hydroxy-16,16-dimethyl-11α,15-bis(tetrahydropyran-2-yloxy)-5-cis,13-trans-prostadienoic acid in place of 16-(3-chlorophenoxy)-9α-hydroxy-16-methyl-11α,15α-bis(tetrahydropyran-2-yloxy)-18,19,20-trinor-5-cis,13-trans-prostadienoic acid.

The compounds shown in the following table were prepared in a similar manner to that described above by using the appropriate substituted phenol or pyridinol in the ether formation reaction.

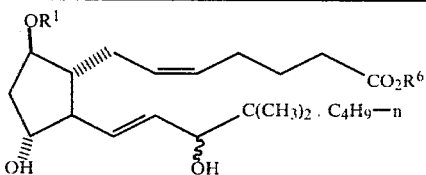

| R[1] | R[6] | R_F | Mass spectrum of per-(trimethylsilyl) derivative of more polar C-15 epimer | |
|---|---|---|---|---|
| | | | Found | Calculated |
| 4-acetamidophenyl | $CH_3$ | 0.41[a] 0.52[a] | 673.4188 | 673.4192 |
| 3-dimethylaminophenyl | $CH_3$ | 0.34[b] 0.49[b] | 659.4399 | 659.4399 |
| 5-chloro-2-pyridyl | H | 0.40[a] 0.58[a] | 709.3769 | 709.3778 |

[a] ethyl acetate
[b] 1:1 v/v ethyl acetate/toluene

EXAMPLE 3

A solution of methyl 9β,16-bis(3-chlorophenoxy)-11α,15α-dihydroxy-16-methyl-18,19,20-trinor-5-cis,13-trans-prostadienoate, (9 mg.) in anhydrous tetrahydrofuran was stirred for 16 hours with lithium borohydride (3.3 mg.). Saturated aqueous sodium hydrogen tartrate (0.5 ml.) was then added and the mixture was extracted with ethyl acetate (3×2 ml.). The combined ethyl acetate solutions were dried and the solvent was evaporated. The residue was purified by preparative layer chromatography to yield 9β,16-bis(3-chlorophenoxy)-16-methyl-18,19,20-trinor-5-cis,13-trans-prostadien-1,11α,15α-triol as a colourless gum, $R_F = 0.55$ (ethyl acetate). The n.m.r. spectrum in hexadeuterioacetone had the following characteristic signals (δvalues):

6.75–7.40, 8H, multiplet, aromatic protons
5.75, 2H, multiplet, trans-olefinic protons
5.44, 2H, multiplet, cis-olefinic protons
4.55, 1H, multiplet, >C$\underline{H}$.OC$_6$H$_4$Cl
3.80–4.24, 2H, multiplet, >C$\underline{H}$(OH)
3.45, 2H, triplet, —C$\underline{H}_2$OH

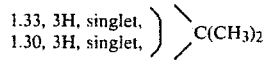

1.33, 3H, singlet,
1.30, 3H, singlet, } >C(CH$_3$)$_2$

The mass spectrum of the tris(trimethylsilyl) derivative had (M-methyl)$^+$ = 749.3015. Calculated for $C_{38}H_{59}O_5Cl_2Si_3 = 749.3045$.

EXAMPLE 4

A solution of the more polar C-15 epimer of methyl 11α,15-dihydroxy-9β-phenoxy-5-cis,13-trans-prostadienoate (26 mg.) in methanol (3 ml.) was stirred with 1 N aqueous sodium hydroxide (0.35 ml.) for 16 hours and the solvent was then evaporated. The residue was dissolved in water (1 ml.) and acidified to pH 1 by the dropwise addition of 1 N hydrochloric acid, and the aqueous phase was extracted with ethyl acetate (3×5 ml.). The combined ethyl acetate solutions were dried and the solvent was evaporated. The residue was purified by preparative layer chromatography to yield the more polar C-15 epimer of 11α,15-dihydroxy-9β-phenoxy-5-cis,13-trans-prostadienoic acid as a colourless gum, $R_F = 0.32$ (3:1 v/v ethyl acetate/toluene). The n.m.r. spectrum in hexadeuterioacetone had the following characteristic signals (δ values):

6.74–7.35, 5H, multiplet, aromatic protons
5.66, 2H, multiplet, trans-olefinic protons
5.40, 2H, multiplet, cis-olefinic protons
4.44, 1H, multiplet, >C$\underline{H}$(OPh)
3.90–4.30, 2H, multiplet, >C$\underline{H}$(OH)

The mass spectrum of the tris(trimethylsilyl) derivative had $M^{30} = 646.3935$. Calculated for $C_{35}H_{62}O_5Si_3 = 646.3904$.

The more polar C$_{15}$ epimer of methyl 11α,15-dihydroxy-9β-phenoxy-5-cis,13-trans-prostadienoate used as starting material was prepared as follows:

7-[2β-dimethoxymethyl-5α-hydroxy-3α-(tetrahydropyran-2-yloxy)-cyclopent-1α-yl]hept-5-cis-enoic acid (14.81 g.) was treated for 5 minutes with an excess of ethereal diazomethane. The ether and excess reagent were distilled off on a water bath at 50° C. to give the methyl ester, methyl 7-[2β-dimethoxymethyl-5α-hydroxy-3α-(tetrahydropyran-2-yloxy)-cyclopent-1α-yl]hept-5-cis-enoate, as an oil, $R_F = 0.77$ (9:1 v/v methylene chloride/methanol).

A solution of the above methyl ester (14.94 g.), triphenylphosphine (19.6 g.) and phenol (7.0 g.) in anhydrous tetrahydrofuran (125 ml.) was stirred during the dropwise addition of diethyl azodicarboxylate (13.7 g., 95% pure) whilst maintaining the temperature below 30° C. After a further one hour, the solvent was evaporated and the residue was chromatographed on a "Florisil" (200 g.) column, eluting with toluene to yield the phenyl ether, methyl 7-[2β-dimethoxymethyl-5β-phenoxy-3α-(tetrahydropyran-2-yloxy)cyclopent-1α-yl]hept-5-cis-enoate, $R_F = 0.90$ (5% v/v methanol in methylene chloride), contaminated with phenol.

A solution of the above mixture of the phenyl ether and phenol (32.0 g.) and toluene-p-sulphonic acid monohydrate (0.18 g.) in methanol (100 ml.) was stirred for 1 hour. Pyridine (0.54 ml.) was then added and the solvent was evaporated. The residue was partitioned between ethyl acetate (3×50 ml.) and brine (25 ml.). The combined ethyl acetate solutions were dried and the solvent was evaporated, and the residue was dried azeotropically by the evaporation of added anhydrous toluene, to give the crude ester alcohol, methyl 7-(2β-dimethoxymethyl-3α-hydroxy-5β-phenoxycyclopent-1α-yl)hept-5-cis-enoate, $R_F = 0.28$ (1:1 v/v ethyl acetate/toluene). The n.m.r. spectrum in deuteriochloroform of a small sample, purified by preparative layer chromatography, had the following characteristic signals (δ values):

6.75–7.40, 5H, multiplet, aromatic protons
5.47, 2H, multiplet, cis-olefinic protons

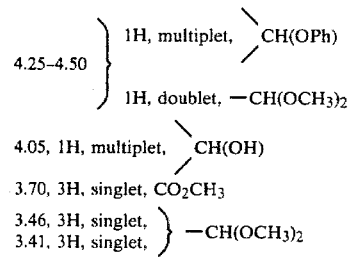

4.25–4.50 { 1H, multiplet, >CH(OPh)
1H, doublet, —CH(OCH$_3$)$_2$ 4.05, 1H, multiplet, >CH(OH)

3.70, 3H, singlet, CO$_2$CH$_3$ 3.46, 3H, singlet,
3.41, 3H, singlet, } —CH(OCH$_3$)$_2$ The crude ester alcohol (29.5 g.) was dissolved in a mixture of anhydrous toluene (200 ml.) and pyridine (15.9 ml.) and stirred for 16 hours with 4-phenylbenzoyl chloride (20.3 g.). Water (1.8 ml.) and pyridine (8.0 ml.) were then added and stirring was continued for a further 24 hours. Ethyl acetate (200 ml.) was then added and the mixture was extracted with saturated aqueous sodium bicarbonate (5×200 ml.). The whole mixture was filtered through "Hyflo" (trade mark) kieselguhr when necessary during the extraction to remove precipitated sodium 4-phenylbenzoate. The organic phase was then washed with brine (100 ml.) and dried, and the solvent was evaporated to yield the crude 4-phenylbenzoate ester, methyl 7-[2β-dimethoxymethyl-5β-phenoxy-3α-(4-phenylbenzoyloxy)cyclopent-1α-yl]-hept-5-cis-enoate as a brown gum, $R_F=0.56$ (3:2 v/v toluene/ethyl acetate). A 3.0 g. sample of this crude 4-phenylbenzoate ester was purified by column chromatography on "Florisil" (300 g.) eluting with toluene.

The 4-phenylbenzoate ester (900 mg.) was vigorously stirred for 20 minutes in a two-phase system consisting of 2% v/v isopropanol in chloroform (46 ml.) and concentrated hydrochloric acid (23 ml.). The chloroform layer was separated and the aqueous layer was extracted with chloroform (46 ml.). The organic layers were combined, washed successively with aqueous saturated sodium bicarbonate (40 ml.) and brine (20 ml.) and dried, and the solvent was evaporated to give the aldehyde, methyl 7-[2β-formyl-5β-phenoxy-3α-(4-phenylbenzoyloxy)cyclopent-1α-yl]-hept-5-cis-enoate, a pale yellow oil, $R_F=0.42$ (3:2 v/v toluene/ethyl acetate).

A solution of the aldehyde (219 mg.) and dimethyl 2-oxoheptylphosphonate (130 mg.) in 9:1 v/v toluene/t-butanol (10 ml.) was stirred vigorously for 16 hours with 1 N aqueous sodium hydroxide (542 µl.). Glacial acetic acid (50 µl.) was then added and the mixture was partitioned between ethyl acetate (3×10 ml.) and brine (5 ml.). The combined organic solutions were dried, the solvent was evaporated, and the residue was chromatographed on a "Florisil" (5 g.) column, eluting with 9:1 v/v toluene/ethyl acetate, to yield the enone, methyl 15-oxo-9β-phenoxy-11α-(4-phenylbenzoyloxy)-5-cis,13-trans-prostadienoate, $R_F=0.68$ (4:1 v/v toluene/ethyl acetate).

The enone (200 mg.) was dissolved in 3 ml. of a 0.36 M solution of di-isobornyloxyaluminium isopropoxide and left for 3 hours. Saturated aqueous sodium hydrogen tartrate (5 ml.) and ethyl acetate (10 ml.) were added, and the mixture was stirred vigorously for 10 minutes. The two phases were then separated and the aqueous phase was extracted with a further 10 ml. of ethyl acetate. The combined organic phases were dried and the solvent was evaporated. The residue was chromatographed on a silica gel M.F.C. (10 g.) column, eluting initially with toluene to remove the isoborneol and then with ethyl acetate, to give the enol, methyl 15-hydroxy-9β-phenoxy-11α-(4-phenylbenzoyloxy)-5-cis,13-trans-prostadienoate, $R_F=0.22$ (5% v/v ethyl acetate in toluene).

A solution of the enol (115 mg.) in anhydrous methanol (10 ml.) was stirred for 16 hours with powdered anhydrous potassium carbonate (127 mg. The solution was then neutralised with glacial acetic acid and the methanol was evaporated. The residue was partitioned between ethyl acetate (2×10 ml.) and water (5 ml.), then combined organic extracts were dried and the solvent was evaporated. Preparative layer chromatography of the crude product gave the separated C-15 epimers of the required starting material, methyl 11α,15-dihydroxy-9β-phenoxy-5-cis,13-trans-prostadienoate, $R_F=0.28$ and 0.44 (1:1 v/v ethyl acetate/toluene).

EXAMPLE 5

|  | % w/v |
|---|---|
| 16-(3-Chlorophenoxy)-11α,15α-dihydroxy-16-methyl-9β-phenoxy-18,19,20-trinor-5-cis,13-trans-prostadienoic acid | 0.0037 |
| Sodium phosphate B.P. | 2.90 |
| Sodium acid phosphate B.P. | 0.30 |
| Water for injection | to 100 |

The sodium phosphate B.P. was dissolved in about 80% of water, followed by the prostadienoic acid derivative, and when dissolved, the sodium acid phosphate B.P. The solution was made up to volume with water for injection, and the pH was checked to be between 6.7 and 7.7. The solution was filtered to remove particulate matter, sterilised by filtration and filled into pre-sterilised neutral glass ampoules under aseptic conditions.

The prostane derivative may, of course, be replaced by an equivalent amount of another prostane derivative of the invention.

EXAMPLE 6

The process described in Example 5 was repeated, omitting the sodium phosphate B.P. and sodium acid phosphate B.P., to give ampoules containing a sterile aqueous solution of 16-(3-chlorophenoxy)-11α,15α-dihydroxy-16-methyl-9β-phenoxy-18,19,20-trinor-5-cis,13-trans-prostadien-9α,11α,15-triol which are used in the manner described in Example 5.

The prostane derivative may be replaced by an equivalent amount of another prostane derivative of the invention, to give other sterile aqueous solutions.

EXAMPLE 7

The process described in Example 4 was repeated using methyl 16-(3-chlorophenoxy)-11α,15-dihydroxy-9β-phenoxy-17,18,19,20-tetranor-5-cis, 13-trans-prostadienoate in place of methyl 11α,15-dihydroxy-9β-phenoxy-5-cis,13-trans-prostadienoate, to give the C-15 epimers of 16-(3-chlorophenoxy)-11α,15-dihydroxy-9β-phenoxy-17,18,19,20-tetranor-5-cis,13-trans-prostadienoic acid, $R_F=0.43$ and 0.48 (ethyl acetate). The n.m.r. spectrum in hexadeuterioacetone of the more polar C-15 epimer had the following characteristic signals (δ values):

6.75–7.35, 9H, multiplet, aromatic protons
5.75, 2H, multiplet, trans-olefinic protons
5.45, 2H, multiplet, cis-olefinic protons
4.46, 1H, multiplet, >C$\underline{H}$(OPh)
4.00, 2H, doublet, C$\underline{H}_2$OAromatic The mass spectrum of the tris(trimethylsilyl) derivative of the more polar C-15 epimer had M+ =716.3130. Calculated for $C_{37}H_{57}O_6Si_3Cl=716.3150$.

The methyl ester used as starting material was prepared by the process described in the second part of Example 4, using dimethyl [3-(3-chlorophenoxy)-2-oxopropyl]phosphonate in place of dimethyl 2-oxoheptylphosphonate.

EXAMPLE 8

A solution of the more polar C-15 epimer of methyl 11α,15-dihydroxy-16,16-dimethyl-9β-phenoxy-4-cis,13- trans-prostadienoate (24 mg.) in methanol (4 ml.) was stirred with 1 N aqueous sodium hydroxide (0.4 ml.) for 16 hours and the solvent was then evaporated. The residue was dissolved in water (1 ml.) and acidified to pH 1 by the dropwise addition of 1 N hydrochloric acid, and the aqueous phase was extracted with ethyl acetate (3×5 ml.). The combined ethyl acetate solutions were dried and the solvent was evaporated. The residue was purified by preparative layer chromatography to yield the more polar C-15 epimer of 11α,15-dihydroxy-16,16-dimethyl-9β-phenoxy-4-cis,13-trans-prostadienoic acid as a colourless gum, $R_F=0.25$ (ethyl acetate). The n.m.r. spectrum in hexadeuterioacetone had the following characteristic signals (δ values):

6.75–7.35, 5H, multiplet, aromatic protons
5.60, 2H, multiplet, trans-olefinic protons
5.40, 2H, multiplet, cis-olefinic protons
4.50, 1H, multiplet >C$\underline{H}$(OPh)
3.70–4.20, 2H, 2 multiplets, >C$\underline{H}$(OH)

0.90, 3H, singlet,
0.86, 3H, singlet,   $\rangle$C(CH$_3$)$_2$

The mass spectrum of the tris(trimethylsilyl) derivative had (M-methyl)$^-$ = 659.3994 Calculated for C$_{36}$H$_{63}$O$_5$Si$_3$ = 659.3984.

The more polar C$_{15}$ epimer of methyl 11α,15-dihydroxy-16,16-dimethyl-9β-phenoxy-4-cis,13-trans-prostadienoate used as starting material was prepared as follows:

A solution of 2α-allyl-3β-dimethoxymethyl-4α-(tetrahydropyran-2-yloxy)cyclopentan-1α-ol (10.5 g.), triphenylphosphine (18.3 g.) and phenol (6.6 g.) in anhydrous tetrahydrofuran (150 ml.) was stirred during the dropwise addition of diethyl azodicarboxylate (15.1 g., 95% pure) whilst maintaining the temperature below 30° C. After a further one hour, the solvent was evaporated and the residue was chromatographed on a "Florisil" (375 g.) column, eluting with 1:1 v/v ethyl acetate/toluene to yield the phenyl ether, 2α-allyl-3β-dimethoxymethyl-1β-phenoxy-4α-(tetrahydropyran-2-yloxy)cyclopentane as an oil.

To a solution of the phenyl ether (6.72 g.) in dry tetrahydrofuran (200 ml.) under an atmosphere of argon at 0° C. was added 32 ml. of a 1 M solution of borane in tetrahydrofuran. After one hour, water (32 ml.), 1 N sodium hydroxide (32 ml.) and 30% w/v hydrogen peroxide (10 ml.) were added successively at 0° C. The mixture was then allowed to warm to room temperature and stirred for 2½ hours. The reaction mixture was again cooled to 0° C., the excess hydrogen peroxide was destroyed by the slow dropwise addition of aqueous sodium metabisulphite, and the mixture was extracted with methylene chloride (3×50 ml.). The combined organic extracts were washed successively with saturated aqueous sodium bicarbonate and brine, and were then dried, and the solvents were evaporated to give the primary alcohol, 3-[2β-dimethoxymethyl-5β-phenoxy-3α-(tetrahydropyran-2-yloxy)cyclopent-1α-yl]propanol as an oil, $R_F=0.39$ (1:1 v/v ethyl acetate/toluene).

A solution of the primary alcohol (2.5 g.) in anhydrous methylene dichloride (50 ml.) was added to a stirred solution of Collins' reagent (75 ml.), [prepared from chromium trioxide (4.5 g.) and pyridine (7.3 ml.) in anhydrous methylene dichloride (113 ml.)]. After 15 minutes at room temperature, the mixture was poured onto a column of "Florisil" (75 mg.) and eluted with methylene dichloride to give the aldehyde, 3-[2β-dimethoxymethyl-5β-phenoxy-3α-(tetrahydropyran-2-yloxy)cyclopent-1α-yl]propionaldehyde as an oil, $R_F=0.64$ (1:1 v/v ethyl acetate/toluene).

Finely powdered (3-carboxypropyl)triphenylphosphonium iodide (7.32 g.) was heated to 100° C. under vacuum for 1 hour. The evacuated vessel was filled with an atmosphere of argon, the solid was dissolved in dimethyl sulphoxide (15 ml.) and the solution was cooled to room temperature. To this solution was added 11.15 ml. of a 2 M solution of methanesulphinylmethyl sodium in dimethyl sulphoxide, followed by a solution of the aldehyde described above (1.9 g.) in dimethyl sulphoxide (20 ml.). The solution was stirred for 30 minutes and the solvent was evaporated under reduced pressure at a temperature below 40° C. The residue was shaken with water (40 ml.) and extracted with ether (5×40 ml.), and the extracts were discarded. The aqueous solution was acidified to pH 3–4 with 2 N aqueous oxalic acid, and extracted with diethyl ether (4×120 ml.). The extracts were combined, washed with saturated brine and dried, and evaporation of the solvents gave the acid, 7-[2β-dimethoxymethyl-5β-phenoxy-3α-(tetrahydropyran-2-yloxy)cyclopent-1α-yl]hept-4-cis-enoic acid as a clear oil, $R_F=0.37$ (1:1 v/v ethyl acetate/toluene).

To a solution of the acid (1.16 g.) in ether (30 ml.) at 0° C. was added an excess of a solution of diazomethane in ether. After 10 minutes, the ether and excess reagent were distilled off on a water bath at 50° C. to give the methyl ester, methyl 7-[2β-dimethoxymethyl-5β-phenoxy-3α-(tetrahydropyran-2-yloxy)cyclopent-1α-yl]hept-4-cis-enoate, as a clear oil, $R_F=0.79$ (1:1 v/v ethyl acetate/toluene).

A solution of the above methyl ester (1.28 g.) and toluene-p-sulphonic acid monohydrate (90 mg.) in methanol was stirred for 4 hours. Pyridine (270 μl.) was added, the solvent was evaporated, and the residue was dried azeotropically by the evaporation of added anhydrous toluene, to give the crude ester alcohol, methyl 7-(2β-dimethoxymethyl-3α-hydroxy-5β-phenoxycyclopent-1α-yl)hept-4-cis-enoate, $R_F=0.53$ (1:1 v/v ethyl acetate/toluene).

The crude ester alcohol (1.28 g.) was dissolved in a mixture of anhydrous toluene (12 ml.) and pyridine (0.54 ml.) and stirred for 16 hours with 4-phenylbenzoyl chloride (728 mg.). Water (2 ml.) was then added and stirring was continued for a further one hour. Ethyl acetate (20 ml.) was then added and the mixture was extracted with saturated aqueous sodium bicarbonate (5×20 ml.). The whole mixture was filtered through "Hyflo" kieselguhr when necessary during the extraction to remove precipitated sodium 4-phenylbenzoate. The organic phase was then washed with brine (10 ml.) and dried, and the solvent was evaporated. The residue was chromatographed on a dry column of "Kieselgel 60" (300 g.), eluting with 4:1 v/v toluene/ethyl acetate, to yield the 4-phenylbenzoate ester, methyl 7-[2β-dimethoxymethyl-5β-phenoxy-3α(4-phenylbenzoyloxy)cyclopent-1α-yl]]-hept-4-cis-enoate as an amorphous solid, $R_F=0.60$ (4:1 v/v toluene/ethyl acetate). The n.m.r. spectrum in deuteriochloroform had the following characteristic signals (δ values):

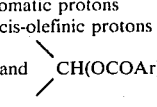

```
6.75-8.25, 14H, multiplet, aromatic protons
5.30-5.70, 3H, multiplet  ⎫ cis-olefinic protons
                          ⎬ and  >CH(OCOAr)
                          ⎭
4.45, 1H, doublet, —CH(OCH₃)₂
4.40-4.70, 1H, multiplet, >CH(OPh)
3.60, 3H, singlet, —CO₂CH₃
3.41, 3H, singlet, ⎫ —CH(OCH₃)₂
3.39, 3H, singlet, ⎭
```

The 4-phenylbenzoate ester (286 mg.) was vigorously stirred for 20 minutes in a two-phase system consisting of 2% v/v isopropanol in chloroform (14.7 ml.) and concentrated hydrochloric acid (7.35 ml.). The chloroform layer was separated and the aqueous layer was extracted with chloroform (15 ml.). The organic layers were combined, washed successively with aqueous saturated sodium bicarbonate (15 ml.) and brine (8 ml.) and dried. The solvent was evaporated to give the aldehyde, methyl 7-[2β-formyl-5β-phenoxy-3α-(4-phenylbenzoyloxy)cyclopent-1α-yl]-hept-4-cis-enoate, a pale yellow oil, $R_F=0.50$ (9:1 v/v toluene/ethyl acetate).

A solution of the aldehyde (280 mg.) and dimethyl 3,3-dimethyl-2-oxoheptylphosphonate (210 mg.) in 9:1 v/v toluene/t-butanol (15 ml.) was stirred vigorously for 16 hours with 1 N aqueous sodium hydroxide (780 μl.). Glacial acetic acid (50 μl.) was then added and the mixture was partitioned between ethyl acetate (3×10 ml.) and brine (5 ml.). The combined organic solutions were dried, the solvent was evaporated, and the residue was chromatographed on a "Florisil" (75 g.) column, eluting with 9:1 v/v toluene/ethyl acetate, to yield the enone, methyl 16,16-dimethyl-15-oxo-9β-phenoxy-11α-(4-phenylbenzoyloxy)-4-cis,13-trans-prostadienoate, $R_F=0.57$ (9:1 v/v toluene/ethyl acetate).

The enone (231 mg.) was dissolved in 5 ml. of a 0.36 M solution of di-isobornyloxyaluminium isopropoxide and left for 16 hours. Saturated aqueous sodium hydrogen tartrate (8 ml.) and ethyl acetate (10 ml.) were added, and the mixture was stirred vigorously for 10 minutes. The two phases were then separated and the aqueous phase was extracted with a further 10 ml. of ethyl acetate. The combined organic phases were dried and the solvent was evaporated. The residue was chromatographed on a silica gel M.F.C. (10 g.) column, eluting initially with toluene to remove the isoborneol and then with ethyl acetate, to give the enol, methyl 15-hydroxy-16,16-dimethyl-9β-phenoxy-11α-(4-phenylbenzoyloxy)-4-cis,13-trans-prostadienoate, $R_F=0.36$ (9:1 v/v toluene/ethyl acetate).

A solution of the enol (137 mg.) in anhydrous methanol (10 ml.) was stirred for 16 hours with powdered anhydrous potassium carbonate (233 mg.). The solution was then neutralised with glacial acetic acid and the methanol was evaporated. The residue was partitioned between ethyl acetate (2×10 ml.) and water (5 ml.), the combined organic extracts were dried and the solvent was evaporated. Preparative layer chromatography of the crude product gave the separated C-15 epimers of the required starting material, methyl 11α,15-dihydroxy-16,16-dimethyl-9β-phenoxy-4-cis,13-trans-prostadienoate, $R_F=0.11$ and 0.19 (4:1 v/v toluene/ethyl acetate).

EXAMPLE 9

The process described in Example 8 was repeated, using methyl 16-(3-chlorophenoxy)-11α,15-dihydroxy-16-methyl-9β-phenoxy-18,19,20-trinor-4-cis,13-trans-prostadienoate in place of methyl 11α,15-dihydroxy-16,16-dimethyl-9β-phenoxy-4-cis,13-trans-prostadienoate, to give the more polar C-15 epimer of 16-(3-chlorophenoxy)-11α,15-dihydroxy-16-methyl-9β-phenoxy-18,19,20-trinor-4-cis,13-trans-prostadienoic acid, $R_F=0.29$ (ethyl acetate). The n.m.r. spectrum in hexadeuterio acetone had the following characteristic signals (δ values):

6.75–7.40, 9H, multiplet, aromatic protons
5.75, 2H, multiplet, trans-olefinic protons
5.35, 2H, multiplet, cis-olefinic protons
4.50, 1H, multiplet, >C$\underline{H}$(OPh)
3.90–4.30, 2H multiplet, >C$\underline{H}$(OH)
1.25, 6H, singlet, >C(C$\underline{H}$₃)₂

The mass spectrum of the tris(trimethylsilyl) derivative had (M-methyl)⁺ = 729.3229; Calculated for $C_{38}H_{58}O_6Si_3Cl = 729.3230$.

The methyl ester used as starting material was prepared by the process described in the second part of Example 8, using dimethyl [3-(3-chlorophenoxy)-3-methyl-2-oxopropyl]phosphonate in place of dimethyl 3,3-dimethyl-2-oxoheptylphosphonate.

What we claim is:
1. A prostane derivative of the formula:

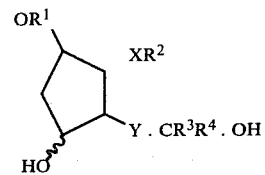

wherein:
R¹ is a phenyl or naphthyl radical optionally substituted by one or more halogen atoms, amino, carboxy, hydroxy, hydroxymethyl, nitro, phenyl or trifluoromethyl radicals, 1–4C alkyl, alkoxy, or alkanoylamino radicals, 2–5C alkoxycarbonyl or di(-1–3C alkyl)amino radicals, or a pyridyl, quinolyl, indolyl, benzo[b]furanyl, benzo[b]thienyl, pyridazinyl, pyrimidinyl or pyrazinyl radical optionally substituted by one or more halogen atoms or 1–4C alkyl radicals;
X is a hexa-1,6-diyl, hex-2-en-1,6-diyl, hexa-2,5-dien-1,6-diyl, hexa-3,5-dien-1,6-diyl, hex-3-en-1,6-diyl or hex-5-trans-en-1,6-diyl radical, in each of which C-1 of the hexyl radical is bonded to the cyclopentane ring;
R² is a carboxy, hydroxymethyl, 5-indanyloxycarbonyl, 4-biphenylyloxycarbonyl or 5-tetrazolyl radical;
 a radical of the formula —CO—NHR⁵ wherein R⁵ is a 2–8C alkanoyl radical, a 4–8C cycloalkanoyl radical, a 7–11C aroyl or substituted aroyl radical in which the substituent is a halogen atom or a methyl or methoxy radical, a 1–7C alkylsulphonyl radical or an arylsulphonyl or substituted arylsulphonyl radical in which the substituent is a halogen atom or a methyl or methoxy radical;
 a radical of the formula —CO.OR⁶ wherein R⁶ is a 1–8C alkyl radical, a 4–8C cycloalkyl radical, a phenyl or substituted phenyl radical in which the substituent is 1 to 3 chlorine atoms or 1–4C alkyl radicals, or an ethyl radical substituted in the β-position by 1 to 3 chlorine, bromine or iodine atoms; a radical of the formula —CO.O.CHR$^7$.COR$^8$ wherein R$^7$ is a hydrogen atom or a benzyl radical and R$^8$ is a phenyl, 4-bromophenyl, 4-biphenylyl, 4-nitrophenyl, 4-benzamidophenyl or 2-naphthyl radical;

a radical of the formula —CH$_2$O.CO(NH)$_m$R$^9$ wherein m is 0 or 1 and R$^9$ is a 1-10C alkyl or halogenoalkyl radical, a 2-10C alkoxyalkyl radical, a ω-carboxy-1-6C-alkyl radical or a phenyl or naphthyl radical optionally substituted by one or more halogen atoms, nitro or phenyl radicals or 1-5C alkyl, alkoxy or halogenoalkyl radicals; or a radical of the formula —COOR$^{10}$ wherein R$^{10}$ is:
—W—NH—CO—CH$_3$
—W—NH—CO—Ph
—W—NH—CO—W—NH—CO—CH$_3$
—W—NH—CO—W—NH—CO—Ph
—W—NH—CO—NH$_2$
—W—Ph
—W—C(Ph)$_3$
—W—CH$_2$—CH(CONH$_2$)—NH—CO—CH$_3$
—W—CH$_2$—CH(CONH$_2$)—NH—CO—Ph
—W—CH=N—NH—CO—NH$_2$
—W—CO—CH$_3$
—W—CO—NH$_2$
—W—CO—NH—W—C(Ph)$_3$
—W—COO—CH$_3$
—W—OOC—Ph
—W—OOC—W—NH—CH$_3$

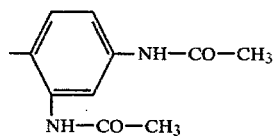

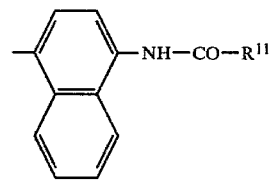

wherein W is a 1,4-phenylene radical and R$^{11}$ is a methyl, phenyl or amino radical;

Y is an ethylene or trans-vinylene radical;
R$^3$ is a hydrogen atom or a 1-4C alkyl radical;
R$^4$ is a 3-8C alkyl radical;

a phenyl, benzyl, phenyl(2-4C alkyl), or phenylethynyl radical optionally substituted in the phenyl ring by one or more halogen atoms, hydroxy, nitro or phenyl radicals, 1-4C alkyl, alkoxy, halogenoalkyl or alkanoylamino radicals, a 2-4C alkenyl or alkenyloxy radicals or di(1-3C alkyl)amino radicals;

a radical of the formula —CR$^{12}$R$^{13}$.OR$^{14}$ wherein R$^{12}$ and R$^{13}$ are each a hydrogen atom or a 1-4C alkyl radical, and R$^{14}$ is a 1-4C alkyl radical or a phenyl or naphthyl radical optionally substituted as defined immediately above;

a radical of the formula —CR$^{12}$R$^{13}$OR$^{15}$, wherein R$^{12}$ and R$^{13}$ have the meanings stated above, or a radical of the formula —R$^{15}$, wherein R$^{15}$ is a radical which is derived from an aromatic 5-membered ring containing one, or two non-adjacent, nitrogen heteroatoms or one nitrogen and one non-adjacent sulphur heteroatoms, or an aromatic fused benzohomologue thereof, or an aromatic 6-membered ring containing one, or two non-adjacent, heteroatoms or a fused benzo-homologue thereof, or from indoline, pyridazine, benzo[b]furan, thiophen or benzo[b]thiophen, which radical is optionally substituted by one or more halogen atoms or 1-4C alkyl radicals;

a radical of the formula —CR$^{12}$R$^{13}$.OR$^{14}$ wherein CR$^{12}$R$^{13}$ together form a 4-6C cycloalkylene radical and R$^{14}$ is a 1-4C alkyl radical or a phenyl or naphthyl radical as defined above; a 4-6C cycloalkyl radical bearing a 1-(2-7C alkyl) substituent; or a radical of the formula:

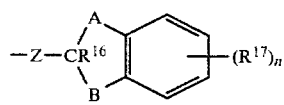

is a direct bond or an alkylidene radical of 1 to 5 carbon atoms; either A is an alkylidene radical of 1 to 5 carbon atoms or an ethylene radical, and B is a direct bond, an oxygen or sulphur atom, or an alkylidene radical of 1 to 5 carbon atoms, or A is an oxygen atom and B is an oxygen atom, an alkylideneoxy radical of 1 to 5 carbon atoms wherein the oxygen atom is linked directly to the benzene ring, or an alkylidene(alkylimino) radical [alkylidene-N(alkyl)-] wherein the alkylidene radical is of 1 to 5 carbon atoms and the alkyl radical is of 1 to 4 carbon atoms, and wherein the nitrogen atom is linked directly to the benzene ring; R$^{16}$ is a hydrogen atom or an alkyl radical of 1 to 4 carbon atoms, or CR$^{16}$ together with an adjacent carbon atom of A or B forms a double bond; R$^{17}$ is a halogen atom, or an alkyl, alkoxy or halogenoalkyl radical of 1 to 3 carbon atoms, and n is 0, 1 or 2;

and for those compounds which contain a carboxy radical, the pharmaceutically acceptable salts thereof.

2. A prostane derivative as claimed in claim 1 wherein R$^1$ is a phenyl, chlorophenyl, fluorophenyl, bromophenyl, iodophenyl, tolyl, acetamidophenyl, dimethylaminophenyl, trifluoromethylphenyl, chloropyridyl, or ethylphenyl radical, X is a hexa-1,6-diyl, hex-2-en-1,6-diyl or hex-3-en-1,6-diyl radical as defined in claim 1, R$^2$ is a carboxy, hydroxymethyl or 2-5C alkoxycarbonyl radical, Y is an ethylene or trans-vinylene radical, R$^3$ is a hydrogen atom or a methyl radical, and R$^4$ is a 3-8C alkyl radical or a radical of the formula —CR$^{12}$R$^{13}$.OR$^{14}$ wherein R$^{12}$ and R$^{13}$ are each a hydrogen atom or a methyl or ethyl radical, and R$^{14}$ is a phenyl or naphthyl radical optionally substituted as defined in claim 1.

3. A prostane derivative as claimed in claim 1 wherein R$^1$ is a phenyl, chlorophenyl, fluorophenyl, trifluoromethylphenyl, acetamidophenyl, dimethylaminophenyl or chloropyridyl radical, X is a hex-2-en-1,6-diyl or hex-3-en-1,6-diyl radical as defined in claim 1, R$^2$ is a carboxy or methoxycarbonyl radical, Y is a trans-vinylene radical, R$^3$ is a hydrogen atom, and R$^4$ is a n-pentyl or 1,1-dimethylpentyl radical or a radical of the formula —CR$^{12}$R$^{13}$OR$^{14}$ wherein R$^{12}$ and R$^{13}$ are each a hydrogen atom or a methyl radical and R$^{14}$ is a chlorophenyl radical.

4. A prostane derivative as claimed in claim 1 which is 16-(3-chlorophenoxy)-11α,15α-dihydroxy-16-methyl-9β-phenoxy-18,19,20-trinor-5-cis,13-trans-prostadienoic acid, 11α,15α-dihydroxy-16,16-dimethyl-9β-phenoxy-5-cis,13-trans-prostadienoic acid, 9β,16-bis(3-chlorophenoxy)-16-methyl-18,19,20-trinor-5-cis,13-trans-prostadien-1,11α,15α-triol, 11α,15α-dihydroxy-9β-phenoxy-5-cis,13-trans-prostadienoic acid, 9β,16-bis(3-chlorophenoxy)-11α,15α-dihydroxy-16-methyl-18,19,20-trinor-5-cis-13-trans-prostadienoic acid or 9β-(5-chloropyrid-2-yloxy)-11α,15-dihydroxy-16,16-dimethyl-5-cis,13-trans-prostadienoic acid, or a methyl ester thereof.

5. A prostane derivative as claimed in claim 1 which is 16-(3-chlorophenoxy)-11α,15α-dihydroxy-16-methyl-9β-phenoxy-18,19,20-trinor-5-cis,13-trans-prostadienoic acid.

6. A pharmaceutical or veterinary composition comprising a prostane derivative as claimed in claim 1 together with a pharmaceutically or veterinarily acceptable diluent or carrier.

* * * * *